(12) United States Patent
Rajasekaran et al.

(10) Patent No.: US 10,531,845 B2
(45) Date of Patent: Jan. 14, 2020

(54) SYSTEMS AND METHODS FOR IMAGE CORRECTION IN AN X-RAY DEVICE

(71) Applicant: GENERAL ELECTRIC COMPANY, Schenectady, NY (US)

(72) Inventors: Prabhu Rajasekaran, Bangalore (IN); Nasir Ahmed Desai, Bangalore (IN); Vinayak Yardi, Bangalore (IN); Sai Kumar Pennujuru, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 291 days.

(21) Appl. No.: 15/721,029

(22) Filed: Sep. 29, 2017

(65) Prior Publication Data

US 2019/0099151 A1   Apr. 4, 2019

(51) Int. Cl.
*A61B 6/00* (2006.01)
*G06T 3/00* (2006.01)
*G06T 7/00* (2017.01)
*A61B 8/08* (2006.01)

(52) U.S. Cl.
CPC .......... *A61B 6/4233* (2013.01); *A61B 6/4405* (2013.01); *A61B 6/4452* (2013.01); *A61B 6/587* (2013.01); *A61B 8/5223* (2013.01); *G06T 3/00* (2013.01); *G06T 7/0012* (2013.01); *A61B 6/4429* (2013.01)

(58) Field of Classification Search
CPC ........... A61B 6/585; A61B 6/587; G06T 3/00
See application file for complete search history.

(56) References Cited

U.S. PATENT DOCUMENTS

| | | | | |
|---|---|---|---|---|
| 6,493,470 | B1* | 12/2002 | Ikeda | G06K 9/3283 382/289 |
| 6,893,157 | B2* | 5/2005 | Arakawa | A61B 6/08 378/205 |
| 2007/0041508 | A1* | 2/2007 | Tubbs | A61B 6/08 378/207 |
| 2013/0051522 | A1* | 2/2013 | Zaiki | A61B 6/0407 378/62 |
| 2015/0265223 | A1* | 9/2015 | Simon | A61B 6/025 378/4 |
| 2016/0174918 | A1* | 6/2016 | Wang | A61B 6/4405 378/63 |

* cited by examiner

*Primary Examiner* — Yara B Green
(74) *Attorney, Agent, or Firm* — Fletcher Yoder, P.C.

(57) ABSTRACT

A method for image correction in a mobile X-ray device includes obtaining an X-ray image corresponding to a region of interest, where the X-ray image includes a projection of the region of interest by an X-ray beam on a detector plane. The method further includes receiving a tilt parameter corresponding to the detector plane. Moreover, the method includes generating a corrected X-ray image based on the X-ray image and the tilt parameter using a perspective projection technique, where the corrected X-ray image corresponds to a projection of the region of interest on a corrected detector plane.

22 Claims, 7 Drawing Sheets

SYSTEMS AND METHODS FOR IMAGE CORRECTION IN AN X-RAY DEVICE

BACKGROUND

Embodiments of the present specification relate generally to a system and method for image correction in an X-ray device, and more specifically to systems and methods for correcting image distortion due to detector tilt in a mobile X-ray device.

Imaging technologies such as X-ray imaging allow non-invasive acquisition of images of internal structures or features of a subject or an object. Digital X-ray imaging systems produce digital data which can be reconstructed into radiographic images. In digital X-ray imaging systems, radiation from a source is directed toward the subject in a medical application, a package or baggage in a security screening application, or a fabricated component in an industrial quality control inspection application. A portion of the radiation passes through the subject/object and impacts a detector. In volumetric imaging systems, such as computed tomography (CT) tomosynthesis or C-arm angiography systems, a portion of the radiation impinges on a detector array having a series of detector elements for each position of the radiation source. Scintillator elements in the detector convert the impinging radiation to light photons that are sensed by photo-detector elements of the detector. The detector includes a matrix of discrete picture elements or pixels and generates output signals based upon the quantity or intensity of the radiation impacting each pixel region. The output signals are subsequently processed to generate an image that may be displayed for review. These images are used to identify and/or examine the internal structures and organs within a patient's body, objects within a package or container, or defects such as cracks within a fabricated component.

Mobile X-ray units are used image incapacitated people at their bedside and also for imaging in intensive care units (ICUs). In mobile X-ray units, placement of the X-ray detector depends on many factors such as, but not limited to, mobility constraints of the subject and other space constraints. Images that are generated using data acquired with detector placement with such constraints disadvantageously result in tilt artefacts. These tilt artefacts adversely affect diagnosis and may result in the need for additional scans, thereby increasing associated costs and time. In case of medical applications, the additional scans also lead to an increase in radiation exposure and inconvenience to the subject.

BRIEF DESCRIPTION

In accordance with one aspect of the present specification, a method for image correction in a mobile X-ray device is presented. The method includes obtaining an X-ray image corresponding to a region of interest, where the X-ray image includes a projection of the region of interest by an X-ray beam on a detector plane. Furthermore, the method includes receiving a tilt parameter corresponding to the detector plane. The method also includes generating a corrected X-ray image based on the X-ray image and the tilt parameter using a perspective projection technique, where the corrected X-ray image corresponds to a projection of the region of interest on a corrected detector plane. A non-transitory computer readable medium including one or more tangible media, where the one or more tangible media include code adapted to perform the method for image correction in a mobile X-ray device is presented.

In accordance with another aspect of the present specification, a mobile X-ray device is presented. The mobile X-ray device includes an image acquisition unit having at least an X-ray source and an X-ray detector, where the image acquisition unit is configured to obtain an X-ray image corresponding to a region of interest, and where the X-ray image includes a projection of the region of interest by an X-ray beam on a detector plane. The mobile X-ray device further includes a detector tilt correction unit communicatively coupled to the image acquisition unit and configured to receive a tilt parameter corresponding to the detector plane and generate a corrected X-ray image based on the X-ray image and the tilt parameter using a perspective projection technique, where the corrected X-ray image corresponds to a projection of the region of interest in a corrected detector plane.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Embodiments of the present specification are directed to systems and methods for correcting image distortion due to detector tilt in a mobile X-ray device/unit. An X-ray image obtained as a projection of an object on a detector plane of a mobile X-ray device may include image distortions. These image distortions may occur due to misalignment of the detector plane with the object and are characterized by a tilt parameter corresponding to the detector plane. The systems and methods aid in generating a corrected X-ray image based on the received X-ray image and the tilt parameter. The corrected X-ray image so generated aids in enhancing identification of a medical condition of an anatomical region of the subject.

Figure 1:
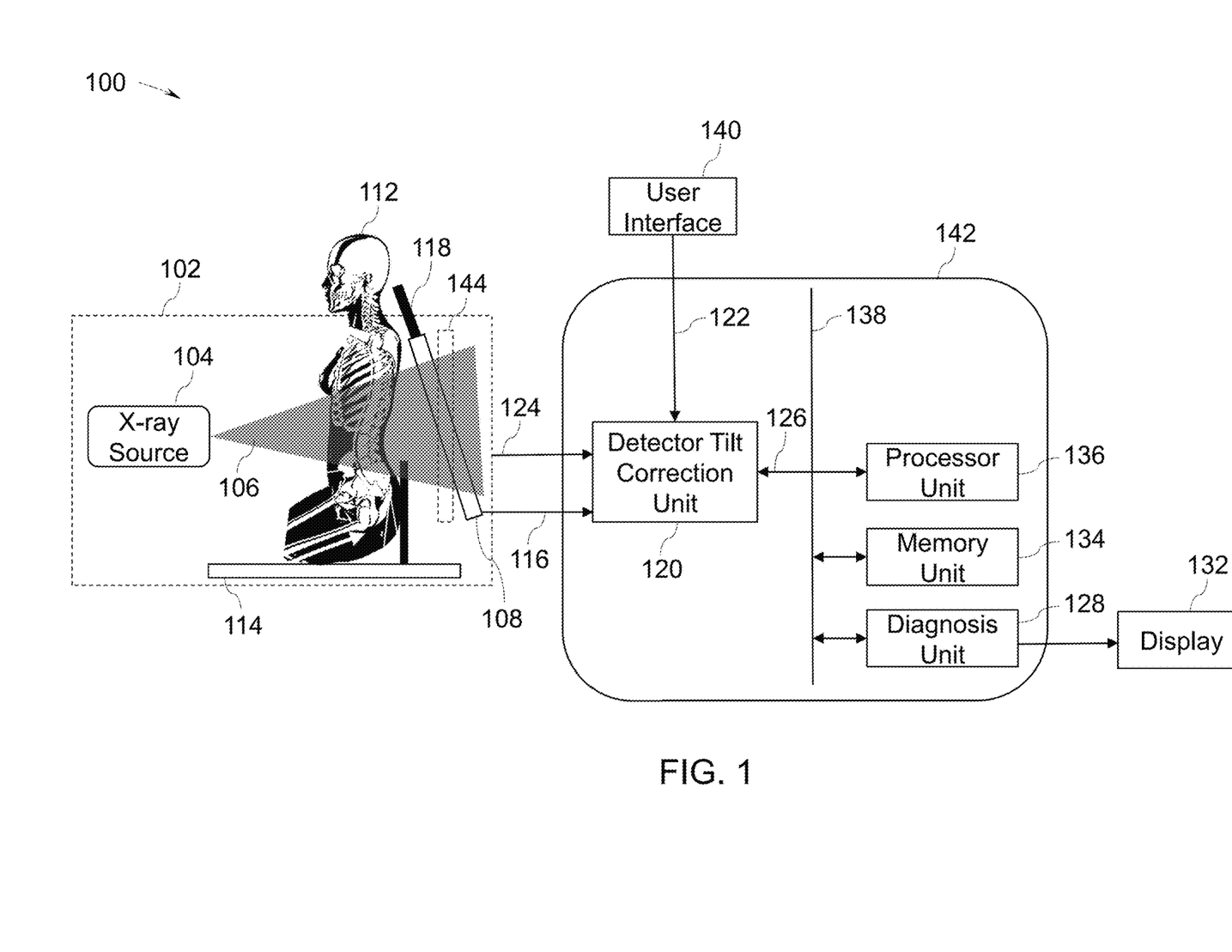
FIG. 1 is a diagrammatic illustration of a mobile X-ray device, in accordance with aspects of the present specification.

FIG. 1 is a diagrammatical illustration of a mobile X-ray device 100, in accordance with aspects of the present specification. In a presently contemplated configuration, the mobile X-ray device 100 includes an image acquisition unit 102 and an image enhancement system 142. The image enhancement system 142 includes a detector tilt correction unit 120, a diagnosis unit 128, a memory unit 134, and a processor unit 136.

The image acquisition unit 102 includes a radiation source such as an X-ray source 104. The X-ray source 104 is configured to emit a radiation beam such as an X-ray beam 106 having a field of view towards an object 110. In the example of FIG. 1, the object 110 is an anatomical region or a region of interest in a subject such as a patient 112. In another example, the object 110 may correspond to a package or a baggage in a security screening application. In yet another example, the object 110 may be a fabricated component in an industrial application.

The mobile X-ray device 100 further includes a patient table 114 configured to support the patient 112. The X-ray beam 106 upon impinging on the anatomical region 110 may be attenuated differently by portions of the anatomical region 110. An X-ray detector 108 that is disposed in the field of view of the X-ray beam 106 acquires the attenuated X-ray beam. The image acquisition unit 102 is further configured to generate an X-ray image 116 corresponding to the object 110 based on the detected X-ray beam. In the example of FIG. 1, the X-ray image 116 is a projection of the anatomical region 110 of the subject 112 in a detector plane 118. The X-ray image 116 includes a plurality of image pixels corresponding to a plurality of image pixel positions in the detector plane 118.

As noted hereinabove, any misalignment between the detector plane 118 and the object 110 results in "tilt image artifacts" in the resulting X-ray image. In accordance with aspects of the present specification, the detector tilt correction unit 120 is configured to detect and correct any tilt image artifacts in the X-ray image 116 to generate a corrected X-ray image. To that end, the detector tilt correction unit 120 is configured to receive the X-ray image 116 generated by the image acquisition unit 102. Additionally, the detector tilt correction unit 120 is also configured to receive a tilt parameter 122 corresponding to the detector plane 118. In one embodiment, the tilt parameter 122 is obtained from a user interface (UI) 140. In another embodiment, the tilt parameter 122 may be generated by automatic processing of a reference image stored in the memory unit 134.

Further, the detector tilt correction unit 120 is also configured to receive one or more imaging parameters 124 from one or more of the image acquisition unit 102, the UI 140, and an operator. The one or more imaging parameters 124 may include a first field of view angle, a second field of view angle, source co-ordinates representative of a position of the X-ray source 104, detector co-ordinates representative of a position of the X-ray detector 108, and combinations thereof. The detector tilt correction unit 120 is configured to generate a corrected X-ray image 126 based on the X-ray image 116, the tilt parameter 122, one or more of the imaging parameters 124. The corrected X-ray image 126 corresponds to a projection of the anatomical region 110 of the subject 112 in a corrected detector plane 144. The corrected X-ray image 126 includes a plurality of corrected pixels corresponding to a plurality of corrected pixel positions in the corrected detector plane 144.

In one embodiment, the detector tilt correction unit 120 is configured to determine a perspective projection of the detector plane 118 in the field of view of the X-ray beam 106 to determine a projection plane. It may be noted that the detector plane 118 includes a plurality of image pixels that corresponds to a plurality of image pixel positions in the detector plane 118. Further, the detector tilt correction unit 120 is configured to rotate the projection plane to the corrected detector plane 144 using a rotation matrix. The corrected detector plane 144 includes a plurality of rotated pixel positions. The detector tilt correction unit 120 is configured to assign the plurality of image pixel values to a plurality of rotated pixel values in the corrected detector plane 144. The plurality of rotated pixels corresponds to the plurality of rotated pixel positions. Moreover, the detector tilt correction unit 120 is configured to interpolate the plurality of rotated pixels to generate the plurality of corrected pixels. The plurality of rotated pixel positions may also be interpolated to generate the plurality of corrected pixel positions.

It may be noted that the projection plane is rotatable in a three-dimensional (3D) space with reference to a pivot axis. The pivot axis includes a first pivot axis parallel to an X-axis of a Cartesian co-ordinate system, a second pivot axis parallel to a Y-axis of the Cartesian co-ordinate system, and a third pivot axis parallel to a Z-axis of the Cartesian co-ordinate system. The tilt parameter 122 includes at least one of a first tilt angle corresponding to the first pivot axis, a second tilt angle corresponding to the second pivot axis, and a third tilt angle corresponding to the third pivot axis. In one embodiment, the X-ray image 116 is transformed by rotating the X-ray image 116 along the first pivot axis by the first tilt angle. In another embodiment, the X-ray image 116 is transformed by rotating the X-ray image 116 along the second pivot axis by the second tilt angle. Additionally, the X-ray image 116 may also be transformed by rotating the X-ray image 116 along the third pivot axis by the third tilt angle. In general, the X-ray image 116 may be transformed by rotating the X-ray image 116 along at least one of the first pivot axis, the second pivot axis and the third pivot axis.

In accordance with aspects of the present specification, the detector tilt correction unit 120 is configured to determine the projection plane by determining homogenous coordinates for each image pixel in the X-ray image 116 based on the one or more imaging parameters 124. Specifically, the detector plane 118 is placed in a projection space determined by the field of view of the X-ray beam 106 using a perspective projection technique. Additionally, use of the perspective projection technique entails adjusting the position of the detector plane 118 in the projection space by shifting along one or more co-ordinate axes. The shifting of the detector plane in the projection space includes adjusting the detector plane dimensions to match dimensions of a projection frustum formed by the X-ray beam 106 in the projection space. In one embodiment, the perspective projection of detector plane to the projection plane is performed by a projection matrix.

Each image pixel position corresponding to the detector plane 118 includes a first X-coordinate value, a first Y-coordinate value, and a first Z-coordinate value. The first X-coordinate value, the first Y-coordinate value, and the first Z-coordinate value are representative of co-ordinates in the Euclidean space. Furthermore, the first X-coordinate value, the first Y-coordinate value, and the first Z-coordinate value are respectively measured along the X-axis, Y-axis, and Z-axis of the Euclidean space.

In one embodiment use of the perspective projection technique entails including a first W-coordinate with each of the plurality of image pixel positions in the detector plane 118. In one example, each W-coordinate may have a value of one. It may be noted that the first w-coordinate is measured along a W-axis. The X-axis, Y-axis, Z-axis, and W-axis form a four-dimensional (4D) homogenous co-ordinate system. In the 4D coordinate system, the first pivot axis coincides with the X-axis, the second pivot axis coincides with the Y-axis, and the third pivot axis coincides with the Z-axis.

Moreover, the perspective projection further includes adjusting the values of the first X-coordinate value, the first Y-coordinate value, the first Z-coordinate value, and the first W-coordinate value via use of the projection matrix. In one example, the perspective projection of an image pixel position is given by:

$$\begin{bmatrix} x_m \\ y_m \\ z_m \\ w_m \end{bmatrix} = \begin{bmatrix} \frac{2n}{r-l} & 0 & \frac{l+r}{l-r} & 0 \\ 0 & \frac{2n}{t-b} & \frac{b+t}{t-b} & 0 \\ 0 & 0 & \frac{-f-n}{f-n} & \frac{-2fn}{f-n} \\ 0 & 0 & -1 & 0 \end{bmatrix} \begin{bmatrix} x_1 \\ y_1 \\ z_1 \\ w_1 \end{bmatrix} \quad (1)$$

where $[x_1, y_1, z_1, w_1]$ is representative of homogenous coordinates of an image pixel position in the detector plane, $[x_m, y_m, z_m, w_m]$ is representative of modified homogenous coordinates of a projected pixel position, n is a near plane z value, f is a far plane z value, l is a near plane left side value, r is a near plane right side value, t is a near plane top side value, and b is a near plane bottom side value.

In another embodiment, processing the homogenous coordinates of a projected pixel includes moving the detector plane 118 in the projection space along the Z-axis to adjust the dimensions of the X-ray image 116 to match the dimensions of the frustum of the field of view of the X-ray beam 106. A modified first z-coordinate $z_m$ is determined based on the movement of the detector plane 118 along the Z-axis. Further, processing the homogenous coordinates includes modifying the first x-coordinate based on the first z-coordinate, the modified first z-coordinate, and the first x-coordinate values. The modified first x-coordinate value is given by:

$$x_m = \frac{z_m}{z_1} x_1 \quad (2)$$

where $x_m$ is the modified x-coordinate value.

The first y-coordinate value is also modified similarly based on the first y-coordinate, the first z-coordinate, and the modified z-coordinate. The modified first y-coordinate value is given by:

$$y_m = \frac{z_m}{z_1} y_1 \quad (3)$$

where, $y_m$ is the modified y-coordinate value.

It may be noted that as depicted in equations (2) and (3), in certain embodiments, a ratio of the modified z-coordinate and the first z-coordinate is employed to determine the modified x-coordinate and the modified y-coordinate. In particular, the x-coordinate and the y-coordinate are respectively multiplied by the ratio of the modified z-coordinate and the first z-coordinate to obtain the modified x-coordinate and the modified y-coordinate respectively.

Similarly, modified homogenous coordinates of a plurality of projected pixel positions corresponding to the detector plane 118 are determined. In one embodiment, each of the modified homogenous coordinates may be scaled by the corresponding first modified w-coordinate to represent the projected pixel position in the Euclidean coordinate system.

Further, the detector tilt correction unit 120 is also configured to determine the plurality of rotated pixel positions corresponding to the corrected detector plane 144. In one embodiment, the projection plane is tilted by at least one of a first tilt angle with respect to the x-axis, a second tilt angle with respect to the y-axis, and a third tilt angle with respect to the z-axis to determine the corrected detector plane 144. Specifically, the plurality of projected pixel positions is multiplied by the rotation matrix to obtain the plurality of rotated pixel positions. Each rotated pixel position among the plurality of rotated pixel positions includes a second x-coordinate value, a second y-coordinate value, and a second z-coordinate value.

In one example, the projection plane is tilted with respect to only the z-axis to determine the corrected detector plane. In this example, the tilt parameter includes a tilt angle that is representative of an angle between the two detector planes 118, 144.

As noted hereinabove, the detector tilt correction unit 120 is configured to determine a rotated pixel position by rotating the projected pixel positions via use of a rotation matrix. In one example, when the projection plane is rotated with reference to the x-axis, the rotation matrix may be represented as:

$$R_x = \begin{bmatrix} 1 & 0 & 0 \\ 0 & \cos\theta & -\sin\theta \\ 0 & \sin\theta & \cos\theta \end{bmatrix} \quad (4)$$

where $\theta$ is the first tilt angle.

The rotation matrix of equation (4) is used to transform a projected pixel position to a corresponding rotated pixel position. As previously noted, each of the plurality of projected pixel positions includes a modified first x-coordinate, a modified first y-coordinate, and a modified first z-coordinate. A column vector having the modified first x-coordinate, the modified first y-coordinate, and the modified first z-coordinate is pre-multiplied by the rotation matrix $R_x$ to compute a column vector having the second x-coordinate, the second y-coordinate, and the second z-coordinate. In other embodiments, the rotation matrix R may be representative of a combined rotation of the projection plane with reference to two or more of the X-axis, the Y-axis, and the Z-axis.

Subsequent to the determination of the plurality of rotated pixel positions, image pixels of the corrected X-ray image may be determined. In one example, pixel values corresponding to the image pixel positions of the detector plane 118 are assigned as pixel values to the corresponding rotated pixel positions to obtain the image pixels of the corrected X-ray image.

Moreover, in an embodiment where the rotated pixel positions are located with uniform spacing, no further processing for determining corrected pixel positions is required. A rotated image is determined based on the plurality of rotated pixel positions. The rotated image is considered as the corrected X-ray image 126. In some embodiments, the rotated pixel positions may not be located with uniform spacing due to rotation of the projection plane along one or more pivot axes. In such embodiments, the detector tilt correction unit 120 is further configured to modify the rotated pixel values of the rotated X-ray image to determine the corrected X-ray image 126. By way of a non-limiting example, the plurality of rotated pixel positions is interpolated to determine the plurality of corrected pixel positions. The term interpolation used herein refers to determining intermediate pixel positions and corresponding pixel values in the rotated X-ray image. In one example, the plurality of rotated pixel values may be resampled using an interpolation technique to obtain the corrected pixel positions. Other examples of interpolation techniques that may be used for resampling the plurality of rotated pixels to determine the corrected pixel positions include, but are not limited to a bicubic interpolation technique, a bilinear sampling technique, a nearest neighborhood sampling technique, and the like.

In one embodiment, a plurality of interpolating techniques corresponding to the plurality of pivot axes may be used to resample the plurality of rotated pixels to determine the corresponding plurality of corrected pixel positions. In one example, a first pixel value corresponding to each pixel position among the plurality of corrected pixel positions may be generated using a first interpolation technique. The first interpolation technique is selected based on each pixel position and the first pivot axis. In addition, a second pixel value corresponding to each pixel position may be determined using a second interpolation technique. The second interpolation technique is selected based on each pixel position and the second pivot axis. The corrected X-ray image 126 is generated based on a plurality of second pixel values corresponding to the plurality of corrected pixel positions.

With continuing reference to FIG. 1, the diagnosis unit 128 is communicatively coupled to the detector tilt correction unit 120 and configured to receive the corrected X-ray image 126 from the detector tilt correction unit 120. The diagnosis unit 128 is configured to identify a medical condition 130 of the anatomical region 110 of the subject 112 based on the corrected X-ray image 126. In one embodiment, the diagnosis unit 128 is configured to display the corrected X-ray image 126, the medical condition 130, or a combination thereof on a display device 132. In certain embodiments, the display device 132 may be integrated with the UI 140.

Additionally, the diagnosis unit 128 may also be configured to generate a plan for surgical intervention, a medication treatment plan, or a combination thereof based on the diagnosed medical condition 130. In some embodiments, the diagnosis unit 128 is configured to display the corrected X-ray image 126 and/or the medical condition 130 in real-time in response to modification of the tilt parameter 122 provided to the detector tilt correction unit 120. In certain embodiments, the detector tilt correction unit 120 is configured to generate the corrected X-ray image 126 based on the X-ray image 116 and a reference image retrieved from a medical database stored in a memory unit 134.

Further, the processor unit 136 is communicatively coupled to the other units 120, 128, 134, 124, 132, 102 via a communications bus 138 and configured to provide computing and control functionalities. The processor unit 136 includes at least one of a general-purpose computer, a GPU, a digital signal processor, and a controller. In other embodiments, the processor unit 136 includes a customized processor element such as, but not limited to, an application-specific integrated circuit (ASIC) and a field-programmable gate array (FPGA). The processor unit 136 may be further configured to receive commands and/or parameters from an operator via the UI 140. In some embodiments, the processor unit 136 may perform one or more functions of at least one of the image acquisition unit 102 and the detector tilt correction unit 120. The processor unit 136 may include more than one processor co-operatively working with each other for performing intended functionalities. The processor unit 136 may also be configured to store (retrieve) contents into (from) the memory unit 134. In one embodiment, the processor unit 136 is configured to initiate and control the functionality of at least one of the image acquisition unit 102 and the detector tilt correction unit 120.

In one embodiment, the memory unit 134 is a random-access memory (RAM), read only memory (ROM), flash memory or any other type of computer readable memory accessible by one or more of the image acquisition unit 102, the detector tilt correction unit 120, the diagnosis unit 128, and the processor unit 136. Also, in certain embodiments, the memory unit 134 may be a non-transitory computer readable medium encoded with a program having a plurality of instructions to instruct at least one of the image acquisition unit 102, the detector tilt correction unit 120, the diagnosis unit 128, and the processor unit 136 to perform a sequence of steps to generate the corrected X-ray image 126. The program may further instruct the display device 132 to present the corrected X-ray image 126 to the user for evaluation of the corrected X-ray image 126.

Implementing the system 100 as described hereinabove provides a robust technique for correcting artifacts in images that are caused due to any misalignment of the detector with respect to the region of interest, thereby enhancing the accuracy of a medical recommendation.

Figure 2:
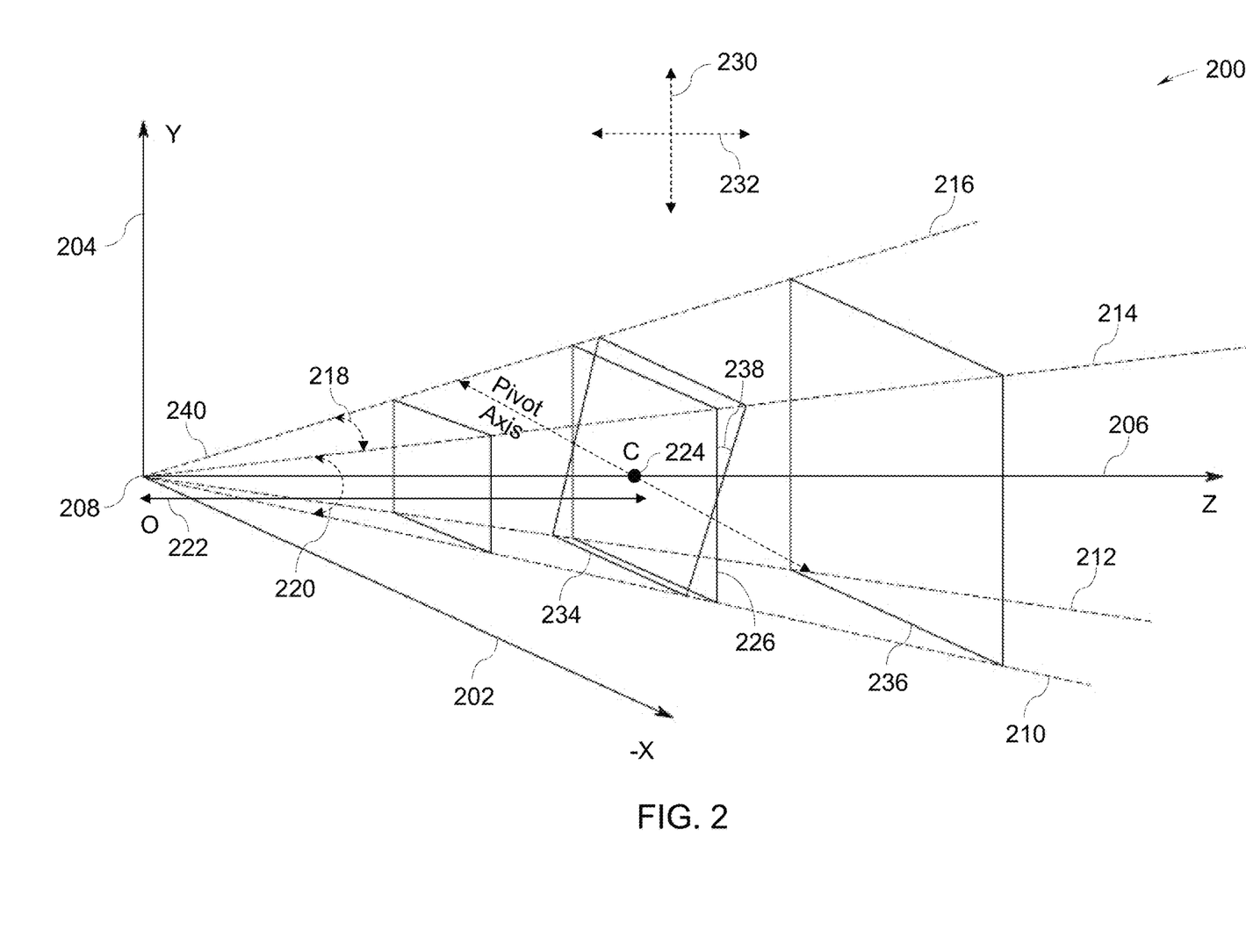
FIG. 2 is a diagrammatical representation of a perspective projection of an X-ray beam used for image correction using the mobile X-ray device of FIG. 1, in accordance with aspects of the present specification.

Referring now to FIG. 2, a diagrammatical representation illustrating a perspective projection 200 of an X-ray beam used for image correction, in accordance with aspects of the present specification, is presented. The perspective projection 200 is illustrated with reference to a Cartesian co-ordinate system having an X-axis 202, a Y-axis 204, and a Z-axis 206. An X-ray source such as the X-ray source 104 (see FIG. 1) is positioned at the origin 208 of the co-ordinate system. In other embodiments, the X-ray source may be positioned at any other location at an offset with respect to the origin 208.

An X-ray beam 240 is emitted by the X-ray source along the Z-axis 206 and the diverging X-ray beam 240 is bound by diverging lines 210, 212, 214, 216. The X-ray beam 240 is characterized by a first field of view angle 218 and a second field of view angle 220 corresponding to the X-ray beam 240. An X-ray image 226 is formed at a source-to-image distance (SID) 222 between the origin 208 and a point 224 on the Z-axis 206. The dimensions of X-ray image 226 increase with an increase in the SID 222. By way of example, an image 236 formed at a greater SID than the SID 222 corresponding to the X-ray image 226 results in the image 236 having greater dimensions when compared to the dimensions of the X-ray image 226. In the illustrated example of FIG. 2, the first field of view angle 218 determines the length of the image formed and the second field of view angle 220 determines the height of the image. The X-ray image 226 has a first pivot axis 228 parallel to the X-axis 202, a second pivot axis 230 parallel to the Y-axis 204, and a third pivot axis 232 parallel to the Z-axis 206. Furthermore, a corrected X-ray image 234 is obtained by tilting the X-ray image 226 around the first pivot axis 228. A first rotation angle 238 that is representative of a tilt parameter is used to generate the corrected X-ray image 234. In other embodiments, the X-ray image 226 may also be rotated simultaneously with reference to the second pivot axis 230 and/or the third pivot axis 232 to generate the corrected X-ray image 234.

Figure 3:
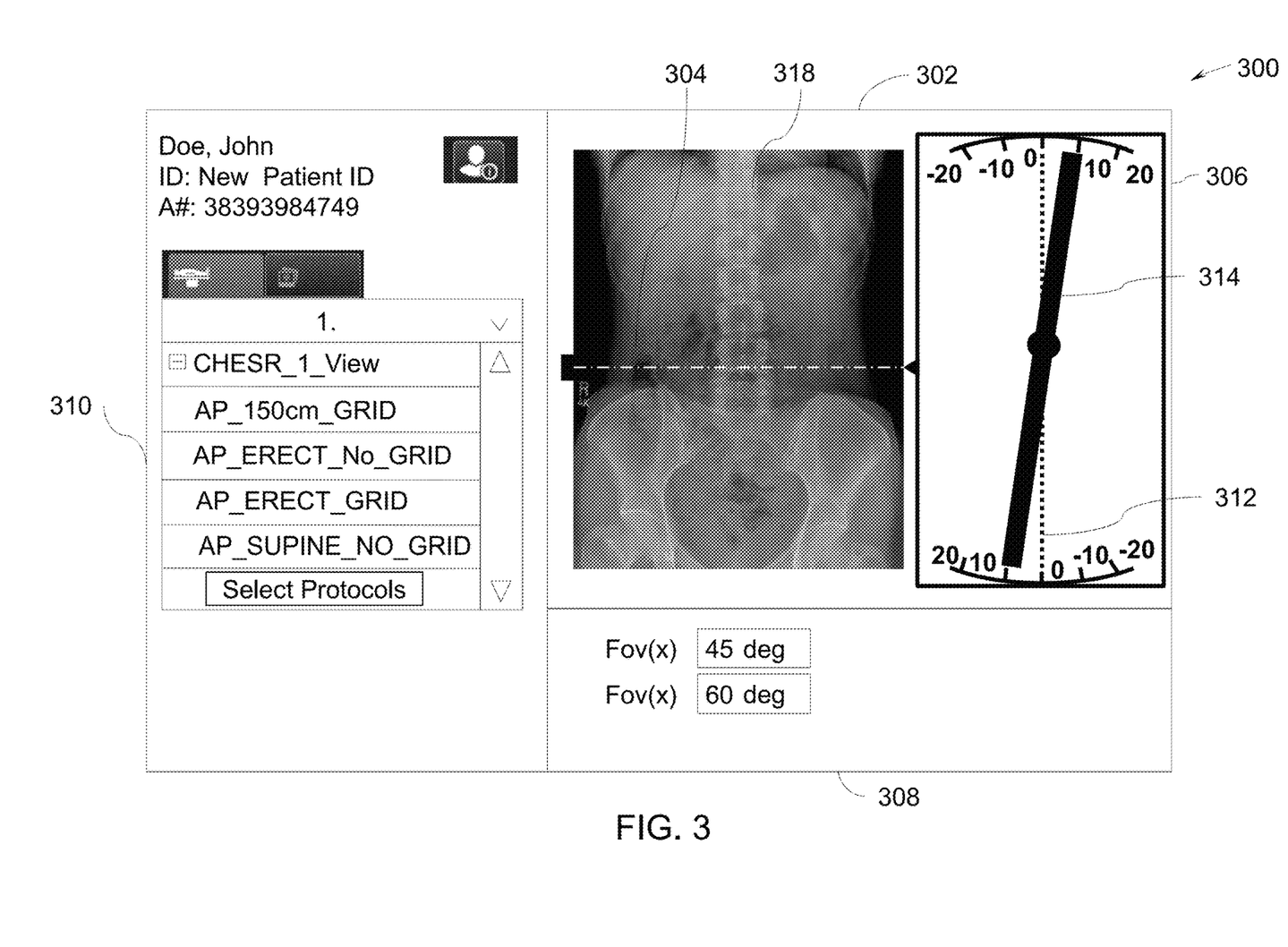
FIG. 3 illustrates one embodiment of a user interface of the mobile X-ray device of FIG. 1, in accordance with aspects of the present specification.

FIG. 3 illustrates one example of a user interface 300 of the mobile X-ray device 100 of FIG. 1, in accordance with aspects of the present specification. In a presently contemplated configuration, the user interface 300 includes a first display area 302, a second display area 306, a third display area 308, and a fourth display area 310. In one example, the first display area 302 may be configured to display at least an X-ray image acquired by the image acquisition unit 102. In addition, a pivot axis 304 may be displayed on the first display area 302. The pivot axis 304 may be moved vertically either using a keyboard or via use of a touch screen interface provided by the user interface 300.

The user interface 300 is also configured to display a tilt angle between a detector plane 312 and a corrected detector plane 314 on the second display area 306. Also, a plurality of imaging parameters used for generating a corrected X-ray image is displayed in the third display area 308. Further, a plurality of other controls such as, but not limited to, patient identification, name, view options, and the like may be visualized in the fourth display area 310.

In one embodiment, the pivot axis 304 may be moved vertically upwards to rotate the X-ray image with respect to the detector plane 312 in a clockwise direction. Similarly, the pivot axis 304 may be moved vertically downwards to rotate the X-ray image with respect to the detector plane 312 in an anti-clockwise direction. A corrected X-ray image 318 generated by the detector tilt correction unit 120 of FIG. 1 may be displayed on the first display area 302. The tilt parameter used for generating the corrected X-ray image is displayed in the second display area 306.

Implementing the user interface 300 as described hereinabove aids a medical professional operating the mobile X-ray device 100 to simultaneously visualize the X-ray image, change the tilt parameter to generate the corrected X-ray image 318, and display the corrected X-ray image 318 in real-time on the user interface 300. In addition, the medical professional is provided with options to further manipulate and/or store the corrected X-ray image 318 in the memory unit 134 of FIG. 1.

Figure 4:
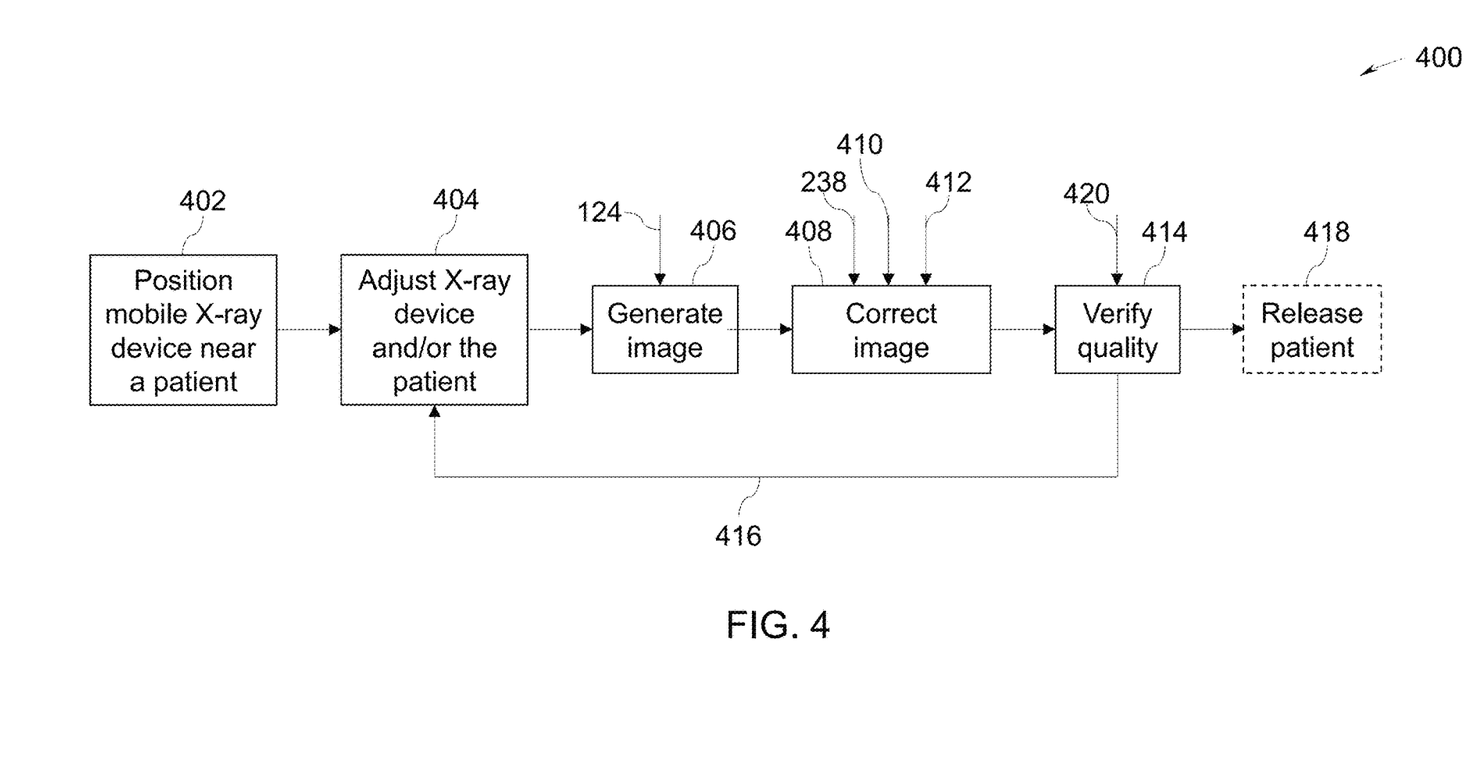
FIG. 4 is a diagrammatical representation of an enhanced digital radiography workflow, in accordance with aspects of the present specification.

Turning now to FIG. 4, an enhanced digital radiography workflow 400, in accordance with aspects of the present specification, is presented. The digital radiography workflow 400 is described with reference to the components of FIGS. 1-3.

The digital radiography workflow 400 is initiated by positioning the mobile X-ray device 100 proximate the patient 112, as indicated by step 402. Further, any adjustments to the mobile X-ray device 100 and/or the position of the patient 112 may be made, as depicted by step 404. At step 406, an X-ray image such as the X-ray image 116 corresponding to an anatomical region 110 in the patient 112 may be generated based on acquired image data that corresponds to the anatomical region of interest 110. One or more imaging parameters 124 may be used for acquiring the X-ray image 116.

In accordance with aspects of the present specification, the X-ray image 116 is processed for correcting distortions introduced by any misalignment between a position of the patient 112 with respect to the X-ray detector 108, as indicated by image correction step 408. In particular, at step 408, the X-ray image 116 is processed by the detector tilt correction unit 120 to corrected any detector tilt related distortions to generate the corrected X-ray image. In one embodiment, the first rotation angle 238 corresponding to the first pivot axis 228 is used for generating the corrected X-ray image. In other embodiments, a second rotation angle 410 corresponding to a second pivot axis such as the second pivot axis 230 and/or a third rotation angle 412 corresponding to a third pivot axis such as the third pivot axis 230 232 may also be used for generating the corrected X-ray image. Consequent to the image correction step 408, a corrected X-ray image such as the corrected X-ray image 126 is generated.

Furthermore, at step 414, a quality of the corrected X-ray image 126 is verified based on one or more image metrics 420. The image metrics 420 may be provided by a medical professional evaluating the corrected X-ray image 126. The medical professional may alter one or more of the first rotational angle 238, the second rotational angle 410, and the third rotation angle 412 to generate an optimal corrected X-ray image. If the quality of the corrected X-ray image is satisfactory, the corrected X-ray image may be stored and the patient may be released, as indicated by step 418.

However, at step 414, if the quality of the corrected X-ray image is not satisfactory, one or more of the first rotation angle 238, the second rotation angle 410, and the third rotation angle 412 are modified and the corrected X-ray image may be reprocessed to regenerate the corrected X-ray image. In certain other embodiments, one or more of the imaging parameters 124 may be changed and the corrected X-ray image may be regenerated.

In accordance with further aspects of the present specification, if the quality of the corrected X-ray image is not satisfactory, the acquisition step 406 may be repeated as illustrated by a reverse path 416. In such a scenario, positions of the patient 112 and/or the X-ray detector 108 may be readjusted and an additional X-ray image may be generated. The additional X-ray image is further processed for image correction to generate the corrected X-ray image. The image correction step 408 within the digital radiography workflow 400 reduces the number of additional X-ray images, and thereby reduces X-ray exposure to the patient 112.

Figure 5A:
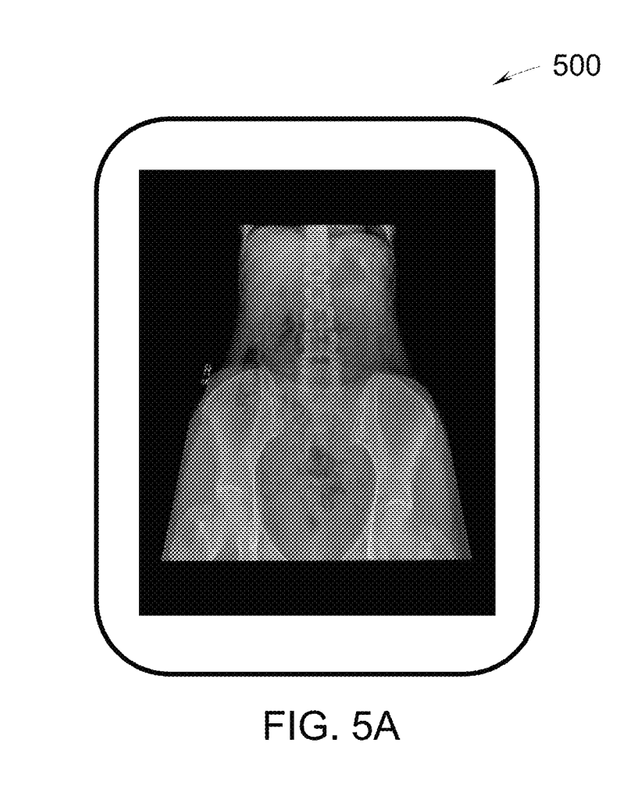
FIGS. 5A-5D are images illustrating image correction using the mobile X-ray device of FIG. 1, in accordance with aspects of the present specification.
Figure 5B:
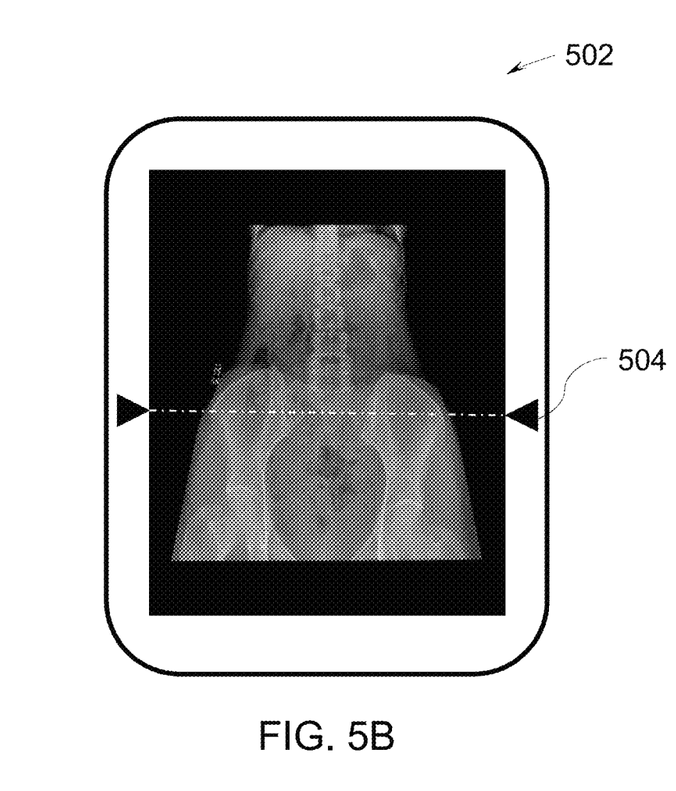

FIGS. 5A-5D are images illustrating image correction using the mobile X-ray device 100 of FIG. 1, in accordance with aspects of the present specification. FIG. 5A is an X-ray image 500 acquired using the image acquisition unit 102 of FIG. 1. FIG. 5B is a corrected X-ray image 502. In particular, the corrected X-ray image 502 is representative of the X-ray image 500 that is rotated with reference to a pivot axis 504 in an anti-clockwise direction. In the example of FIG. 5B, the X-ray image 500 is rotated by about −10 degrees with reference to the pivot axis 504.

Figure 5C:
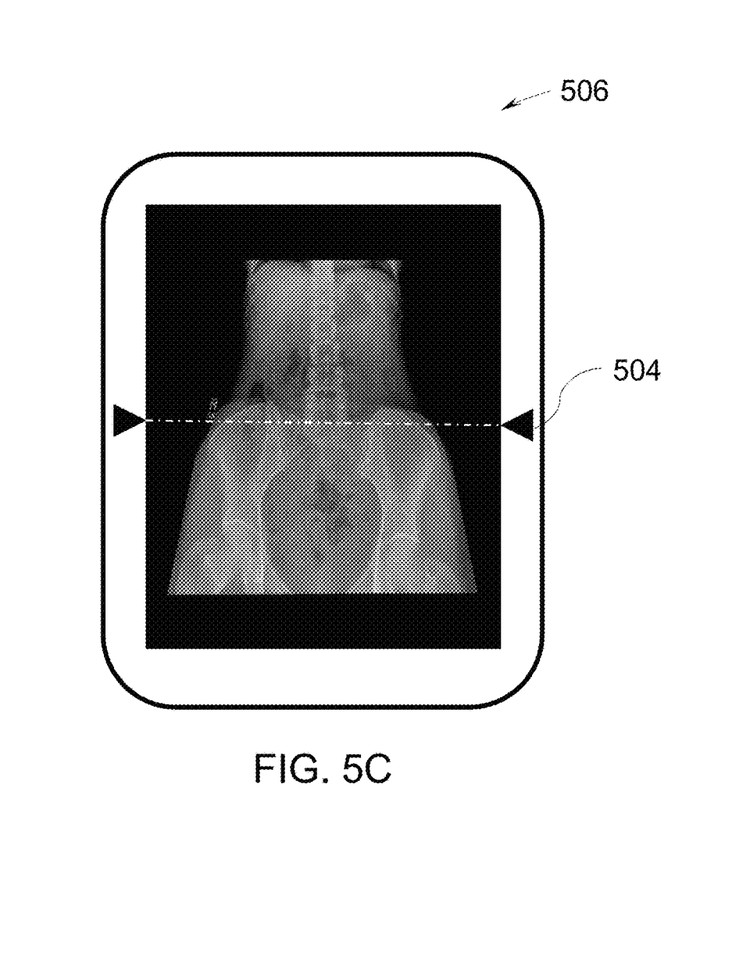
Figure 5D:
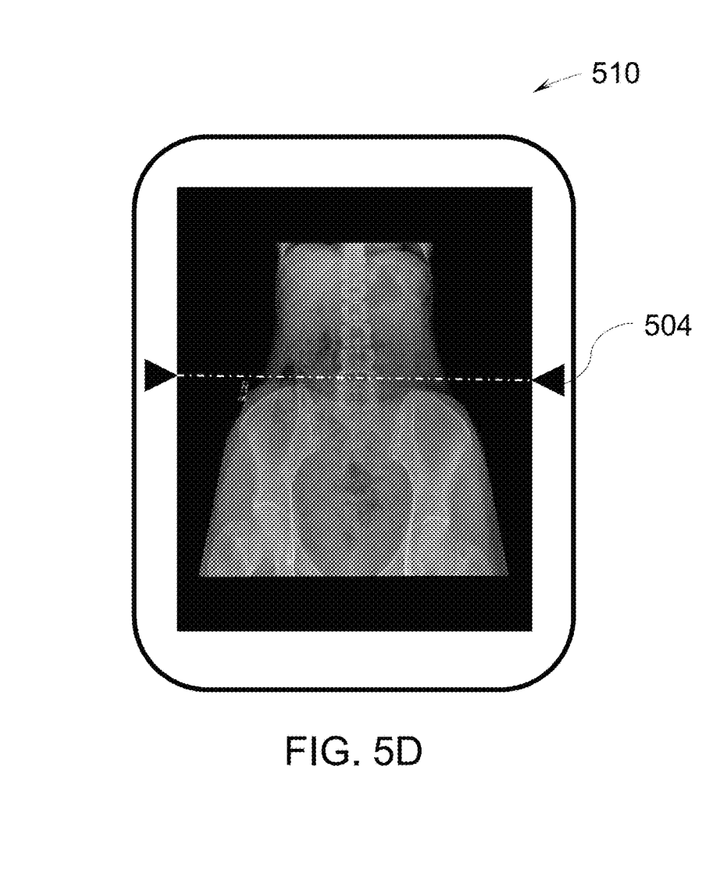

FIG. 5C is a corrected X-ray image 506 with a −20-degree correction. More particularly, the X-ray image 500 is rotated with reference to the pivot axis 504 in an anti-clockwise direction by −20 degrees to generate the corrected X-ray image 506. In a similar fashion, FIG. 5D is a corrected X-ray image 510 with a −30-degree correction. In the example of FIG. 5D, the corrected X-ray image 510 generated by rotating the X-ray image 500 rotated with reference to the pivot axis 504 in an anti-clockwise direction by −30 degrees. It may be noted that while the rotation to generate the corrected X-ray image 502 of FIG. 5B is insufficient to generate an optimal corrected X-ray image, the corrected X-ray image 510 of FIG. 5D is rotated excessively, thereby rendering the X-ray image 510 sub-optimal. The corrected X-ray image 506 of FIG. 5C is optimally rotated and provides an anatomically correct view of the anatomical region 110 in the patient 112.

Figure 6:
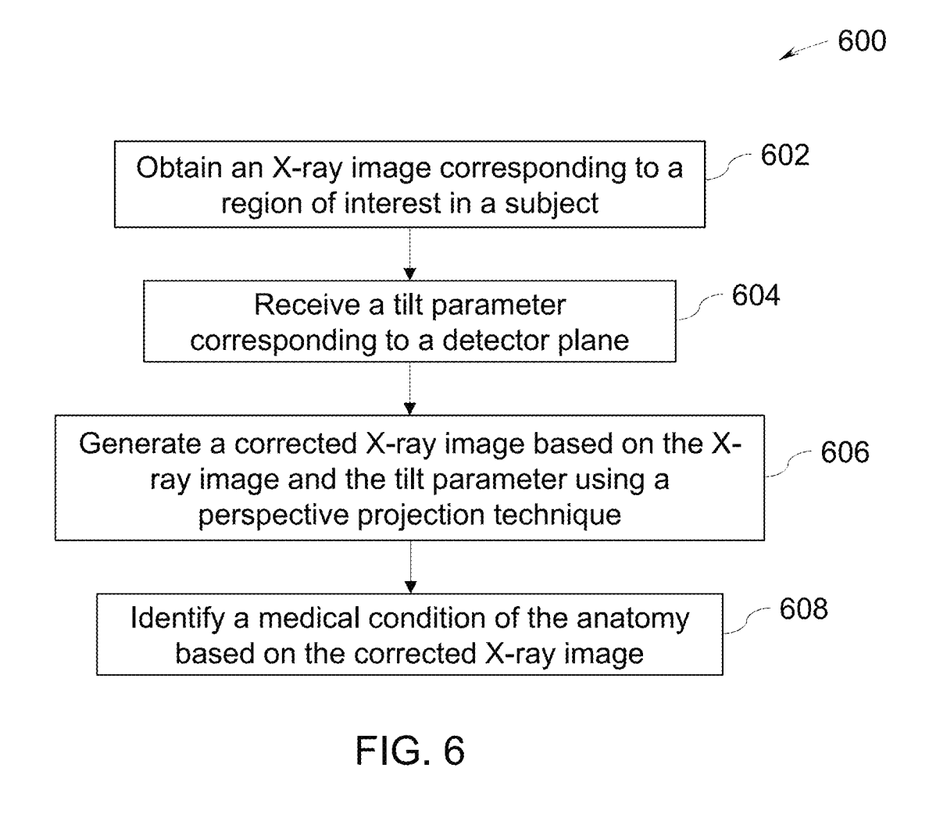
FIG. 6 is a flow chart for a method of image correction in a mobile X-ray device, in accordance with aspects of the present specification.

Referring now to FIG. 6, a flow chart representing a method 600 for image correction in a mobile X-ray device, in accordance with aspects of the present specification, is presented. The method includes obtaining or generating an X-ray image, as indicated by step 602. The X-ray image corresponds to a projection of an anatomical region of a subject in a detector plane in a field of view of an X-ray beam. The method also includes receiving one or more imaging parameters such as, but not limited to, a first field of view angle, a second field of view angle, a position of an X-ray source in the mobile X-ray device, and a position of an X-ray detector in the mobile X-ray device.

Further, at step 604, a tilt parameter corresponding to the detector plane is received. As previously noted, the tilt parameter represents one or more tilt angles with reference to one or more corresponding pivot axes. The detector plane is rotatable in a 3D space with reference to a pivot axis.

Furthermore, at step 606, a corrected X-ray image is generated based on the X-ray image and the tilt parameter using a perspective projection technique. The corrected X-ray image corresponds to a projection of the anatomical region in a corrected detector plane. Generating the corrected X-ray image includes performing perspective projection of the detector plane to a projection plane and adjusting the projection plane to match dimensions of the frustum in a field of view of an X-ray beam. In one embodiment, the detector plane having the X-ray image is positioned in a projection space of the field of view of the X-ray beam to determine the projection plane. Further, the perspective plane in the projection space is adjusted by matching the dimensions of the projection plane to the dimensions of the frustum in the field of view of the X-ray beam.

Generating the corrected X-ray image further includes rotating the adjusted projection plane to obtain the corrected detector plane. The corrected detector plane includes a plurality of rotated pixel positions that correspond to a plurality of image pixel positions of the X-ray image. In one embodiment, the corrected detector plane is obtained by rotating the projection plane using a rotation matrix. In one embodiment, the rotation matrix may correspond to a single pivot axis among the first pivot axis, the second pivot axis, and the third pivot axis and a corresponding tilt angle. In another embodiment, the rotation matrix may correspond to a combined pivot axis and corresponding tilt angles. For example, the rotation matrix may be configured to rotate the X-ray image simultaneously with reference to the first pivot axis by a first tilt angle, the second pivot axis by a second angle, and the third pivot axis by a third tilt angle. A plurality of rotated pixels is generated corresponding to a plurality of pixel values of the X-ray image based on the rotation matrix.

With continuing reference to step 606, image pixel values corresponding to the X-ray image in the detector plane may be assigned to pixel values of the rotated pixel positions in the corrected detector plane. In some embodiments, generating the corrected X-ray image further includes interpolating the rotated pixel positions to determine a plurality of corrected pixel positions. Also, the plurality of rotated pixel values may be interpolated to generate a plurality of corrected pixel values corresponding to the plurality of corrected pixel positions. In certain embodiments, the plurality of rotated pixel values and the plurality of rotated pixel positions may be interpolated using a suitable interpolation technique to generate the plurality of corrected pixel values and the plurality of corrected positions respectively.

In one embodiment, the interpolation technique includes at least one of a bicubic interpolation technique, a bilinear sampling technique, a nearest neighborhood sampling technique, and the like. Moreover, in one embodiment, for generating a corrected pixel, a first interpolation technique may be selected based on a corresponding corrected pixel position and a first pivot axis. A first pixel value is determined based on the first interpolation technique and the rotated X-ray image. A plurality of first pixels is determined corresponding to a plurality of corrected pixel positions based on the rotated X-ray image. Further, a second interpolation technique may be selected based on the corrected pixel position and a second pivot axis. A second pixel value is determined based on the second interpolation technique and the plurality of first pixel values. A plurality of second pixel values is determined corresponding to the plurality of corrected pixel positions based on the plurality of first pixel values. A corrected X-ray image is generated based on the plurality of second pixel values. The method 600 may also include identifying a medical condition of the anatomy based on the corrected X-ray image, as indicated by step 608.

Various embodiments of systems and methods for image correction described hereinabove enable correction of errors in X-ray images that are caused due to misalignment of the detector with respect to the anatomical region of interest being imaged. The systems and methods effect the image correction by tilting the X-ray image in a projection space using homogenous coordinates after image acquisition. Use of these systems and methods provides an opportunity for medical professionals to provide their inputs in real-time for performing correction of the X-ray images. Performing image tilting in projection space ensures higher image resolution and better subjective quality.

The above-described advantages should be regarded as illustrative rather than restrictive. It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method for image correction in a mobile X-ray device, the method comprising:
   obtaining an X-ray image corresponding to a region of interest, wherein the X-ray image comprises a projection of the region of interest by an X-ray beam on a detector plane;
   receiving a tilt parameter corresponding to the detector plane; and
   generating a corrected X-ray image based on the X-ray image and the tilt parameter using a perspective projection technique, wherein the corrected X-ray image corresponds to a projection of the region of interest on a corrected detector plane.

2. The method of claim 1, further comprising identifying a medical condition of the region of interest based on the corrected X-ray image.

3. The method of claim 1, further comprising receiving one or more imaging parameters, wherein the one or more imaging parameters comprise a first field of view angle, a second field of view angle, a position of an X-ray source in the mobile X-ray device, a position of an X-ray detector in the mobile X-ray device, or combinations thereof.

4. The method of claim 3, further comprising visualizing one or more of the X-ray image, the corrected X-ray image, the one or more imaging parameters, the detector plane, the corrected detector plane, and the tilt parameter in real-time on a display device.

5. The method of claim 1, wherein generating the corrected X-ray image comprises selecting a projection plane based on the detector plane using a projection matrix, and wherein the projection plane is a perspective projection of the detector plane in a field of view of the X-ray beam.

6. The method of claim 5, wherein generating the corrected X-ray image comprises determining the corrected detector plane based on the tilt parameter and the projection plane using a rotation matrix, and wherein the corrected detector plane comprises a plurality of rotated pixel positions corresponding to a plurality of image pixel positions in the detector plane.

7. The method of claim 6, wherein the rotation matrix corresponds to at least one of a first pivot axis of the projection plane, a second pivot axis of the projection plane, and a third pivot axis of the projection plane.

8. The method of claim 6, wherein generating the corrected X-ray image comprises assigning a plurality of image pixel values corresponding to the plurality of image pixel positions to a plurality of rotated pixel values corresponding to the plurality of rotated pixel positions.

9. The method of claim 8, wherein generating the corrected X-ray image comprises determining a plurality of corrected pixels corresponding to a plurality of corrected pixel positions in the corrected detector plane based on the plurality of rotated pixel values using an interpolation technique.

10. The method of claim 9, wherein determining the plurality of corrected pixels based on the plurality of rotated pixel values comprises interpolating the plurality of rotated pixel values using the interpolation technique, and wherein the interpolation technique comprises a bicubic interpolation technique, a bilinear sampling technique, a nearest neighborhood sampling technique, or combinations thereof.

11. The method of claim 9, wherein determining the plurality of corrected pixels comprises:
determining a first pixel value corresponding to each corrected pixel position based on a first interpolation technique, wherein the first interpolation technique is selected based on each corrected pixel position and a first pivot axis of the projection plane; and
determining a second pixel value corresponding to each corrected pixel position based on a second interpolation technique, wherein the second interpolation technique is selected based on each corrected pixel position and a second pivot axis of the projection plane.

12. A mobile X-ray device, comprising:
an image acquisition unit comprising at least an X-ray source and an X-ray detector, wherein the image acquisition unit is configured to obtain an X-ray image corresponding to a region of interest, and wherein the X-ray image comprises a projection of the region of interest by an X-ray beam on a detector plane;
a detector tilt correction unit communicatively coupled to the image acquisition unit and configured to:
receive a tilt parameter corresponding to the detector plane; and
generate a corrected X-ray image based on the X-ray image and the tilt parameter using a perspective projection technique, wherein the corrected X-ray image corresponds to a projection of the region of interest in a corrected detector plane.

13. The mobile X-ray device of claim 12, further comprising a diagnosis unit communicatively coupled to the detector tilt correction unit and configured to identify a medical condition of the region of interest based on the corrected X-ray image.

14. The mobile X-ray device of claim 12, wherein the image acquisition unit is further configured to receive one or more imaging parameters, and wherein the one or more imaging parameters comprise a first field of view angle, a second field of view angle, a position of the X-ray source, a position of the X-ray detector, or combinations thereof.

15. The mobile X-ray device of claim 14, further comprising a display device configured to display one or more of the X-ray image, the corrected X-ray image, the one or more imaging parameters, the detector plane, the corrected detector plane, and the tilt parameter in real-time on a display device.

16. The mobile X-ray device of claim 12, wherein the detector tilt correction unit is further configured to select a projection plane based on the detector plane using a projection matrix, and wherein the projection plane is a perspective projection of the detector plane in a field of view of the X-ray beam.

17. The mobile X-ray device of claim 16, wherein the detector tilt correction unit is further configured to determine the corrected detector plane based on the tilt parameter and the projection plane using a rotation matrix, and wherein the corrected detector plane comprises a plurality of rotated pixel positions corresponding to a plurality of image pixel positions in the detector plane.

18. The mobile X-ray device of claim 17, wherein the rotation matrix corresponds to at least one of a first pivot axis of the projection plane, a second pivot axis of the projection plane, and a third pivot axis of the projection plane.

19. The mobile X-ray device of claim 17, wherein the detector tilt correction unit is further configured to assign a plurality of image pixel values corresponding to the plurality of image pixel positions to a plurality of rotated pixel values corresponding to the plurality of rotated pixel positions.

20. The mobile X-ray device of claim 19, wherein the detector tilt correction unit is further configured to determine a plurality of corrected pixels corresponding to a plurality of corrected pixel positions in the corrected detector plane based on the plurality of rotated pixel values using an interpolation technique.

21. The mobile X-ray device of claim 20, wherein the detector tilt correction unit is further configured to:
determine a first pixel value corresponding to each corrected pixel position based on a first interpolation technique, wherein the first interpolation technique is selected based on each corrected pixel position and a first pivot axis of the projection plane; and
determine a second pixel value corresponding to each corrected pixel position based on a second interpolation technique, wherein the second interpolation technique is selected based on each corrected pixel position and a second pivot axis of the projection plane.

22. A non-transitory computer readable medium comprising one or more tangible media, wherein the one or more tangible media comprise code for causing a computer to perform the steps of:
- obtaining an X-ray image corresponding to a region of interest in a subject, wherein the X-ray image comprises a projection of the region of interest by an X-ray beam on a detector plane;
- receiving a tilt parameter corresponding to the detector plane; and
- generating a corrected X-ray image based on the X-ray image and the tilt parameter using a perspective projection technique, wherein the corrected X-ray image corresponds to a projection of the region of interest in a corrected plane.

* * * * *